United States Patent [19]

Subramaniam et al.

[11] Patent Number: 5,550,299
[45] Date of Patent: Aug. 27, 1996

[54] METHOD OF PREPARING 1.1-DIALKOXYCYCLOALKANES

[75] Inventors: Chitoor S. Subramaniam, Kendall Park, N.J.; Thomas V. John, Yardley, Pa.; David Colvin, North Mobile; George W. Bitler, Mobile, both of Ala.

[73] Assignee: Huls America Inc., Somerset, N.J.

[21] Appl. No.: 327,626

[22] Filed: Oct. 24, 1994

Related U.S. Application Data

[62] Division of Ser. No. 70,563, Jun. 1, 1993, Pat. No. 5,401,885.

[51] Int. Cl.$^6$ .................................................. C07C 43/32
[52] U.S. Cl. .......................................... 568/591; 568/594
[58] Field of Search ...................................... 568/594, 591

[56] References Cited

U.S. PATENT DOCUMENTS

| | | | |
|---|---|---|---|
| 2,527,494 | 10/1950 | Copenhaver | 260/615 |
| 2,567,927 | 9/1951 | Erickson | 260/615 |
| 2,786,872 | 11/1957 | Claus et al. | 260/609 |
| 3,121,751 | 7/1964 | Kesslin et al. | 260/615 |
| 3,354,100 | 11/1967 | Kuryla | 260/2.5 |
| 3,641,164 | 2/1972 | Senewald et al. | 260/615 |
| 3,644,423 | 2/1972 | Roswell et al. | 260/304.9 |
| 4,182,910 | 1/1980 | Schmidt et al. | 568/595 |
| 4,226,790 | 10/1980 | Walker | 260/429 |
| 4,304,767 | 12/1981 | Heller et al. | 424/78 |
| 4,785,012 | 11/1988 | Crews et al. | 514/374 |

FOREIGN PATENT DOCUMENTS

| | | |
|---|---|---|
| A-2367041 | 5/1978 | France . |
| A-2394520 | 1/1979 | France . |
| B-1126854 | 4/1962 | Germany . |
| A-1128963 | 10/1968 | United Kingdom . |

OTHER PUBLICATIONS

E. Muller, "Methoden der organischen chemie, BD. VI/3" 1965, Thieme, Stuttgart, Germany, pp. 300–305.

E. Muller, "Methoden der organischen chemie, BD. VI/3" 1965, Thieme, Stuttgart, Germany, pp. 221–227.

S. Patai, "Chemistry of The Functional Groups; Chemistry of Amidines and Imidates," 1975, Wiley, London, pp. 389–394, 471–472.

S. M. McElvain et al., "Ketene Acetals. XXXI. Dimethylketene Ethyleneacetal," J. Am. Chem. Soc., vol. 75, pp. 3993–3996 (1953).

*Primary Examiner*—José G. Dees
*Assistant Examiner*—Dwayne C. Jones
*Attorney, Agent, or Firm*—Abelman, Frayne & Schwab

[57] ABSTRACT

Ortho esters of the structure

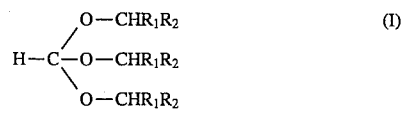

(I)

wherein $R_1$ and $R_2$ are different or the same alkyl moieties and can be a saturated, unsaturated, branched, unbranched or cyclic alkyl moiety of 1–3 carbon atoms, are prepared by first anhydrously reacting hydrogen cyanide or a hydrogen cyanide derivative with a secondary alkanol and hydrogen chloride in the presence of an inert organic solvent. Upon the formation of the resulting imino ether hydrochloride, more secondary alkanol is added to form the ortho esters (I). 1,1-Dialkoxycycloalkanes of the structure

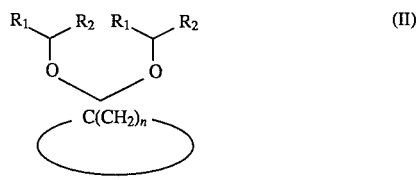

(II)

wherein $R_1$ and $R_2$ correspond to $R_1$ and $R_2$ of structure (I), and n is an integer from 4 to 9, are prepared by reacting with the imino ether hydrochloride more secondary alkanol and a cycloalkanone having 5 to 10 carbon atoms.

8 Claims, No Drawings

METHOD OF PREPARING 1.1-DIALKOXYCYCLOALKANES

This is a divisional of application Ser. No. 08/070,563 filed on Jun. 1, 1993 now U.S. Pat. No. 5,401,885.

BACKGROUND OF THE INVENTION

The present invention relates to a "one-pot" preparation of ortho esters and 1,1-dialkoxycycloalkanes. The ortho esters are compounds of the structure (I)

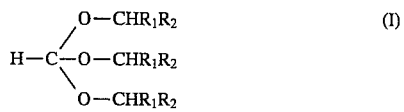

wherein $R_1$ and $R_2$ are different or the same alkyl moieties and can be a saturated, unsaturated, branched, unbranched or cyclic alkyl moiety of 1–3 carbon atoms. The 1,1-dialkoxycycloalkanes are compounds of the structure (II)

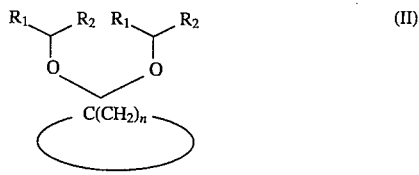

wherein $R_1$ and $R_2$ correspond to $R_1$ and $R_2$ of structure (I), and n is an integer from 4 to 9.

The ortho esters defined by structure (I) are useful water scavengers in organic reaction and solvents. The ortho esters can be used to generate an anhydrous medium for reactions or other processes where the presence of water can be a detriment. The 1,1-dialkoxycycloalkanes defined by structure (II) can be used as protective or blocking structures for the alcohols corresponding to the alkoxy groups. The alcohols can be regenerated under acidic conditions. The compounds defined by structures (I) or (II) are also useful intermediates in the manufacture of pharmaceutical, photographic or agricultural products.

In the process of the invention, compounds of the structure (I) are prepared by first preparing an imino ether hydrochloride by reacting hydrogen cyanide with a secondary alkanol and hydrogen chloride in the presence of an inert organic solvent. Compounds of structure (I) are then prepared by further addition of secondary alkanol to the reaction mixture. Compounds of structure (II) are prepared by the addition of a cycloalkanone and secondary alkanol to the reaction mixture containing the imino ether hydrochloride.

It is known that when an organic acid nitrile is reacted with a primary alcohol and hydrogen chloride, imino ether hydrochloride is formed. This reaction scheme, generally known as the "Pinner" reaction, involves two steps for the preparation of ortho esters. First, an organic acid nitrile, primary alcohol and hydrogen chloride are reacted to prepare an imino ether hydrochloride. Second, the imino ether hydrochloride is separated from the reaction mixture by crystallization, washed for purification, and subsequently subjected to alcoholysis with additional primary alcohol to afford the ortho ester.

Thus, the Pinner reaction is discontinuous by virtue of the purification step and expensive because of the large amount of solvent required. Without the purification step, however, the ortho ester is not formed to a significant extent. Further, in this process, the yield of the ortho ester obtained fluctuates. The ortho ester of the primary alcohol thus obtained can be reacted with a secondary alcohol in the presence of an acid catalyst to obtain the ortho ester of structure (I).

In the method of the invention, however, the preparation of orthoesters of structure (I) is continuous because the purification and transesterification steps are removed. The ortho ester obtained consistently exceeds 70% in yield and 99% in purity.

It is also known that 1,1-dialkoxycycloalkanes can be prepared by reacting cycloalkanones with alcohols in the presence of an acid catalyst. The present invention provides a novel method: cycloalkanone and secondary alkanol are added to a reaction mixture in which an imino ether hydrochloride has been produced.

SUMMARY OF THE INVENTION

The process of the invention is directed to the preparation of ortho esters of the structure (I)

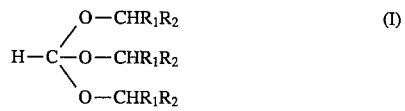

wherein $R_1$ and $R_2$ are different or the same alkyl moieties and can be a saturated, unsaturated, branched, unbranched or cyclic alkyl moiety of 1–3 carbon atoms. The invention also relates to the preparation of 1,1-dialkoxycycloalkanes of the structure (II)

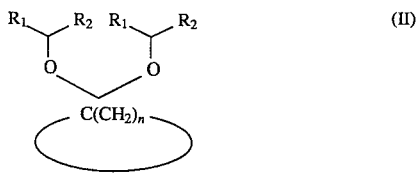

wherein $R_1$ and $R_2$ correspond to $R_1$ and $R_2$ of structure (I), and n is an integer from 4 to 9. Ortho esters of the structure (I) are prepared by first anhydrously reacting hydrogen cyanide, or a derivative of hydrogen cyanide, with a secondary alkanol and hydrogen chloride in the presence of an inert organic solvent. In the reaction mixture, an imino ether hydrochloride of the structure (III) forms

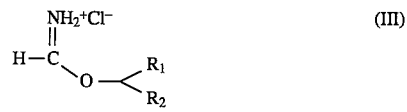

wherein $R_1$ and $R_2$ correspond to $R_1$ and $R_2$ of structure (I). Upon addition of more secondary alkanol, the secondary alkanol will react with the imino ether to form ortho esters of the structure (I). Compounds of the structure (II) are formed by adding to the reaction mixture containing the imino ether of the structure (III) more secondary alkanol and a cycloalkanone having 5 to 10 carbon atoms.

DETAILED DESCRIPTION OF THE INVENTION

The present invention relates to the preparation of orthoformic acid alkyl esters of the structure (I) (described above, hereinafter "ortho esters I") and 1,1-dialkoxycycloalkanes of the structure (II) (described above, hereinafter "dialkoxycycloalkanes II"). The initial step in the preparation of the ortho esters I and the dialkoxycycloalkanes II is the preparation of a reaction mixture containing an imino ether hydrochloride of the structure (III) (described above, hereinafter "imino ether III").

The imino ether III is prepared by anhydrously reacting hydrogen cyanide, or a derivative of hydrogen cyanide, with hydrogen chloride and a secondary alkanol of the structure (IV)

wherein $R_1$ and $R_2$ correspond to $R_1$ and $R_2$ of the ortho esters I. As used herein, the term "alkyl moiety" or "alkyl group" used in reference to $R_1$ and $R_2$ means any alkyl group of 1–3 carbon atoms and includes, without limitation, saturated, unsaturated, branched, unbranched and cyclic alkyl groups.

In the initial reaction, hydrogen cyanide can be replaced with a derivative of hydrogen cyanide. Hydrogen cyanide, however, is preferred. Useful derivatives include compounds of the structure RCN, wherein R is an alkyl group of 1–2 carbon atoms. Useful derivatives include, for example, acetonitrile. Derivatives which include alkyl groups of more than two carbon atoms can slow the reaction appreciably.

The reaction must be carried out under anhydrous conditions. This requirement will be met if the overall content of water in the reaction mixture is lower than the preferable limit of about 1,000 ppm. The reaction mixture should remain anhydrous throughout the preparation of the ortho esters I and the dialkoxycycloalkanes II.

In the preparation of the imino ether III, it is preferable to add the reactants approximately simultaneously to the reaction vessel. While it is sufficient to add approximately equimolar concentrations of the reactants to the reaction vessel a slight excess of the secondary alkanol and hydrogen chloride is preferred. The preferable molar ratio of hydrogen cyanide, or hydrogen cyanide derivative, to secondary alkanol to hydrogen chloride is 1:1.05:1.10. The addition of the reactants can be done in any practical manner, but a continuous addition over a 10 to 12 hour period at a temperature within the range of about 0° C. to 30° C. is preferred. Once the addition is completed, it is preferable to stir the reaction mixture for about 6 to 8 hours at a temperature within the range of about 0° C. to 30° C. Following this process, it is possible to obtain an almost quantitative yield of the imino ether III.

Prior to the addition of the reactants, the reaction vessel should be charged with an organic solvent. A preferred solvent is any solvent which is essentially anhydrous, does not participate in the reaction and does not dissolve ammonium chloride formed as a by-product. Appropriate solvents include, but are not limited to, n-hexane, cyclohexane, heptane, carbon tetrachloride, decalin, petroleum ether, 2,2,4-trimethylpentane, benzene, ethylbenzene, mesitylene, toluene, and xylene, or mixtures thereof. The amount of solvent is preferably at least equal to the molar amount of hydrogen cyanide to be added and, more preferably, more than twice the total molar amount of hydrogen cyanide and secondary alkanol to be added. If the amount of solvent is too low, the slurry which develops during the formation of the imino ether III will not stir effectively.

As stated, it is preferred to carry out the synthesis of the imino ether III at a temperature within the range of about 0° C. to 30° C. Above 30° C., the imino ether III should form but it may subsequently decompose, thereby decreasing the ultimate yield of the ortho ester I or dialkoxycycloalkane II prepared thereafter. Below 0° C., the imino ether III can form but the reaction time may become prohibitively long in duration. A lengthy reaction time would be an obvious detriment in industrial applications. The optimum temperature depends in part on the type of solvent used. With a nonpolar solvent, such as carbon tetrachloride, a temperature within the range of about 10° C. to 20° C. is preferred. With a polar solvent, such as chloroform, a temperature within the range of about 10° C. to 30° C. is preferred.

From the imino ether III, either the ortho ester I or the dialkoxycycloalkane II can be prepared. Separation or purification of the imino ether III, however, is not necessary. Concentration of the reaction mixture under reduced pressure can be done if desired. To prepare the ortho ester I, the imino ether III is subjected to alcoholysis through the addition of more secondary alkanol to the reaction mixture.

Prior to or simultaneously with the addition of the secondary alkanol to prepare the ortho ester I, it is preferred to adjust the pH of the reaction mixture to within the range of about 3 to 5 and, more preferably, to within the range of about 4 to 5. The base employed to adjust the pH should be any basic substance which does not give rise to water. Such basic substances include metallic potassium, metallic sodium, potassium alcoholate, sodium alcoholate, ammonia, methylamine, trimethylamine, ethylenediamine, and diethylenediamine. The preferred base is ammonia gas. If an alcoholate is used, it should be based on the same alcohol as the secondary alcohol employed in the reaction.

If the alcoholysis is carried out outside the preferred pH range of about 3 to 5, the yield of ortho ester I may decrease. If the pH falls below 3, the ortho ester I, which is sensitive to acid, can decompose. If the pH is greater than 5, the imino ether III can become unstable and decompose, thereby lowering the yield of ortho ester I.

It is also preferred to carry out the alcoholysis at a temperature within the range of about 30° C. to 50° C. for a period of about 6 to 12 hours. Although the imino ether III can be unstable above 30° C., in the presence of alcohol, the imino ether III can react to form the ortho ester I in the range of about 30° C. to 50° C. More preferred is a temperature within the range of about 30° C. to 40° C. Below 30° C., the alcoholysis may proceed at a relatively slow rate. Above 50° C., the reaction can still proceed but the imino ether III can begin to decompose, thereby reducing the yield of ortho ester I.

The amount of secondary alkanol to be added to prepare the ortho ester I is preferably at least twice the molar amount of the imino ether III (assuming a quantitative yield). That is, the amount of secondary alkanol to be added is preferably at least twice the molar amount of hydrogen cyanide, or derivative thereof, initially added. Secondary alkanols of the structure (IV) can be used in the process of the invention. Such alkanols include 2-propanol, 2-butanol, 3-methyl-2-pentanol, 2-pentanol, 3-pentanol and 3-heptanol and the like.

In addition to the ortho ester I, the dialkoxycycloalkane II can be prepared from the reaction mixture containing the imino ether III. To the reaction mixture, a cycloalkanone and more secondary alkanol are added. Prior to the addition of each reactant, however, the concentration of hydrogen chloride in the reaction mixture should be adjusted to within the range of about 1% to 5% by weight of the total mixture. The preferred concentration is about 3%.

The reaction mixture can be so adjusted by the addition of a base which does not give rise to water. Such a base is described above. If the concentration of hydrogen chloride exceeds 5%, the ultimate yield of dialkoxycycloalkane II can decrease. If the concentration of hydrogen chloride falls below 1%, the reaction time can become too lengthy.

After the concentration of hydrogen chloride has been adjusted, secondary alkanol is preferably added in an amount at least twice the molar amount of the imino ether III (assuming a quantitative yield). That is, the secondary alkanol is preferably added in an amount at least twice the molar amount of hydrogen cyanide, or hydrogen cyanide derivative, initially added. More preferably, the amount of secondary alkanol added should be between about 2 and 3 times the molar amount of imino ether III.

After or with the addition of the secondary alkanol, a cycloalkanone having a ring structure comprising 5 to 10 carbon atoms is added to the reaction mixture. It is preferred to add the cycloalkanone after the addition of the secondary alkanol. The amount of cycloalkanone to be added is preferably at least equal to the molar amount of imino ether III (assuming a quantitative yield). That is, the amount of cycloalkanone to be added is preferably at least equal to the molar amount of hydrogen cyanide, or derivative thereof, initially added.

The reaction is preferably carried out at a temperature within the range of about 20° C. to 50° C. and, more preferably, at about 40° C. Above 50° C., the dialkoxycycloalkanes II may decompose to an olefinic ether. Below 20° C., the reaction may proceed too slowly. The reaction is preferably carried out, within the preferred temperature range, at a pH of about 2–3 for a period of about 10 to 24 hours and, more preferably, for about 18 hours.

It is preferred to carry out the preparation of both the ortho esters I and dialkoxycycloalkanes II under vacuum to minimize the potential loss of hydrogen chloride and hydrogen cyanide from the system.

After the preparation of the ortho ester I or the dialkoxycycloalkane II, either reaction product can be separated from the reaction mixture, as is further explained below. The reaction mixture should first be cooled to a temperature of about 25° C., and preferably to below 10° C. and filtered to remove the ammonium chloride which forms as a by-product.

To the filtrate, a base should be added to raise the pH to a level greater than about 7 and preferably within the range of about 8 to 10. Basic substances which can be used to raise the pH include alkali metals, such as potassium and sodium, alcoholates, methylamine, ethylenediamine, diethylenediamine and aqueous caustic solution. If aqueous caustic solution is used, the organic phase should be separated prior to separation of the ortho ester I or the dialkoxycycloalkane II to minimize the potential decomposition of either product.

The ortho ester I or dialkoxycycloalkane II can then be obtained by distillation. When the secondary alkanol is present in the reaction mixture, the ortho ester I or dialkoxycycloalkane II remains stable even in the presence of ammonium chloride. If the secondary alkanol is a low-boiling alcohol, and evaporates during the filtration of the ammonium chloride, either the ortho ester I or the dialkoxycycloalkane II can become unstable. Thus, it is preferable to carry out the filtration under conditions which would inhibit the removal of the secondary alkanol. For example, carrying out the filtration at a relatively cool temperature should be effective.

The following examples further illustrate the process of the invention.

EXAMPLE 1

Preparation of 1,1,1-Triisopropylorthoformate

A one liter, 5 necked flask was equipped with an overhead stirrer, thermometer, addition funnel, gas inlet tube, and vacuum outlet through a manostat. Anhydrous toluene was charged into the flask and the system was evacuated with a water aspirator to about 20–22 inches Hg. The entire reaction was carried out under vacuum in order to minimize the loss of hydrogen chloride and hydrogen cyanide from the system. The addition funnel was connected to a mixture of hydrogen cyanide (27.0 g) and 2-propanol (63.0 g). This mixture was named the "mixed feed". The toluene in the flask was cooled to about 10°–15° C., and hydrogen chloride was bubbled through at a rate so as to maintain the system under vacuum. When about 10% of the hydrogen chloride was added, addition of the mixed feed began. The remainder of the hydrogen chloride and mixed feed was added, and reaction mixture stirred, at a rate sufficient to maintain the temperature of the mixture within the range of about 10° C. to 20° C. The addition was done over a four hour period. The imino ether hydrochloride salt crystallized out of the reaction mixture.

The temperature was maintained below 20° C. to prevent decomposition of the imino ether hydrochloride. After the addition, the reaction was stirred for about 8 hours at 20°–25° C. Gaseous ammonia was then added to adjust the pH to 4–5 and neutralize the excess hydrogen chloride, during which time the temperature was maintained around 20° C. 2-propanol (150.0 g) was then added in one lot. The temperature of the mixture was raised and maintained at 30°–35° C. for about 10 hours. Ammonium chloride was filtered off, and the organic phase was washed with a 25% aqueous caustic solution (50 ml). The organic phase was separated from the aqueous phase and distilled under reduced pressure (10 mm Hg). 135 g (70% yield) of 1,1,1-triisopropylorthoformate was obtained, with a purity of at least 98% as determined by gas chromatographic assay.

EXAMPLE 2

Preparation of 1,1-(Dipropan-2'-oxy)cyclohexane

A one liter, 5 necked flask, equipped as in Example 1, was charged with toluene, hydrogen cyanide, hydrogen chloride and isopropyl alcohol in the manner and amounts disclosed in Example 1. A reaction mixture containing an imino ether hydrochloride salt was obtained in accord with Example 1. Gaseous ammonia was used to neutralize excess hydrogen chloride in the mixture to a level of about 3–5%. During the neutralization, the temperature was maintained at 15°–20° C. The mixture was then charged with 2.5 equivalent of 2-propanol relative to the imino ether hydrochloride and 1 equivalent of cyclohexanone. The reactants were added simultaneously. The temperature was allowed to reach about 23° C. before external heating was applied to maintain the temperature at about 40° C. for about 24 hours. The ammonium chloride was filtered off and the organic phase was washed with a 25% caustic solution (50 ml). The organic phase was separated from the aqueous phase and 1,1-(dipropan-2'-oxy)cyclohexane was isolated by distillation. 75 g (50% yield) was obtained with a purity of at least 98% as determined by gas chromatographic assay.

EXAMPLE 3

Preparation of Tri(2-pentyl)orthoformate

A one liter, 5-necked flask is equipped as in example 3. Anhydrous toluene (2 mole equivalents) is charged into the flask and the system is evacuated with a water aspirator to about 20–22 inches Hg. The entire reaction is carried out under vacuum. The addition funnel is charged with a mixture of hydrogen cyanide (27.0 g) and 2-pentanol (92.4 g). This mixture is the "mixed feed". The toluene in the flask is stirred and cooled to about 10°–15° C., and hydrogen chloride is bubbled through at a rate so as to maintain the system under vacuum. When about 10% of the hydrogen chloride is added, addition of the mixed feed is commenced. The remainder of the hydrogen chloride and mixed feed is added, and the reaction mixture stirred, at a rate sufficient to maintain the temperature of the reaction mixture within 10°–20° C. The addition is done over a four hour period. The imino ether hydrochloride salt crystallizes out of the reaction mixture. The temperature is maintained below 20° C. to prevent decomposition of the imino ether hydrochloride. After the addition, the reaction is stirred for about 20 hours at 20°–25° C. The reaction mixture is cooled to 15° C. and gaseous ammonia is added to adjust the pH to 4–5 and neutralize the excess hydrogen chloride. 2-Pentanol (220.0 g) is then added in one lot. The temperature of the reaction mixture is raised and maintained at 40°–50° C. for about 12 hours. Ammonium chloride is filtered off, and the organic phase is washed with a 25% aqueous caustic solution (50 ml). The organic phase is separated from the aqueous phase and distilled under reduced pressure (5 mm Hg) to yield tri(2pentyl)orthoformate.

EXAMPLE 4

Preparation of Tri(3-pentyl)orthoformate

A one liter, 5-necked flask is equipped as in example 3. Anhydrous toluene (2 mole equivalents) is charged into the flask and the system is evacuated with a water aspirator to about 20–22 inches Hg. The entire reaction is carried out under vacuum. The addition funnel is charged with a mixture of hydrogen cyanide (27.0 g) and 3-pentanol (92.4 g). This mixture is the "mixed feed". The toluene in the flask is stirred and cooled to about 10°–15° C., and hydrogen chloride is bubbled through at a rate so as to maintain the system under vacuum. When about 10% of the hydrogen chloride is added, addition of the mixed feed is commenced. The remainder of the hydrogen chloride and mixed feed is added, and the reaction mixture stirred, at a rate sufficient to maintain the temperature of the reaction mixture within 10°–20° C. The addition is done over a four hour period. The imino ether hydrochloride salt crystallizes out of the reaction mixture. The temperature is maintained below 20° C. to prevent decomposition of the imino ether hydrochloride. After the addition, the reaction is stirred for about 20 hours at 20°–25° C. The reaction mixture is cooled to 15° C. and gaseous ammonia is added to adjust the pH to 4–5 and neutralize the excess hydrogen chloride. 3-Pentanol (220.0 g) is then added in one lot. The temperature of the reaction mixture is raised and maintained at 50°–60° C. for about 12 hours. Ammonium chloride is filtered off, and the organic phase is washed with a 25% aqueous caustic solution (50ml). The organic phase is separated from the aqueous phase and distilled under reduced pressure (5 mm Hg) to yield tri(3-pentyl)orthoformate.

EXAMPLE 5

Preparation of 1,1-(Dipentan-2'-oxy)cyclodecane

A one liter, 5-necked flask, equipped as in example 3, is charged with toluene, hydrogen chloride, hydrogen cyanide and 2-pentanol in the manner and amounts disclosed in Example 7. A reaction mixture containing an imino ether hydrochloride salt is obtained in accord with Example 7. Gaseous ammonia is used to neutralize the excess hydrogen chloride in the mixture to a level of about 3–5%. During the neutralization, the temperature is maintained at 15°–20° C. The mixture is then charged with 2.5 equivalents of 2-pentanol relative to the imino ether hydrochloride and 1 equivalent of cyclodecanone. The reactants are added simultaneously. The temperature is allowed to reach about 25° C. before external heating is applied to maintain the temperature at about 40° C. for about 24 hours. The ammonium chloride is filtered off and the organic phase is washed with a 25% caustic solution (50 ml). The organic phase is separated from the aqueous phase and 1,1-(dipentan-2'-oxy)cyclodecane is isolated by distillation under reduced pressure.

EXAMPLE 6

Preparation of 1,1(Dipentan-3'-oxy)cyclooctane

A one liter, 5-necked flask, equipped as in Example 3, is charged with toluene, hydrogen chloride, hydrogen cyanide and 3-pentanol in the manner and amounts disclosed in Example 8. A reaction mixture containing an imino ether hydrochloride salt is obtained in accord with Example 8. Gaseous ammonia is used to neutralize the excess hydrogen chloride in the mixture to a level of about 3–5%. During the neutralization, the temperature is maintained at 15°–20° C. The mixture is then charged with 2.5 equivalents of 3-pentanol relative to the imino ether hydrochloride and 1 equivalent of cyclooctanone. The reactants are added simultaneously. The temperature is allowed to reach about 25° C. before external heating is applied to maintain the temperature at about 40° C. for about 24 hours. The ammonium chloride is filtered off and the organic phase is washed with a 25% caustic solution (50 ml). The organic phase is separated from the aqueous phase and 1,1-(dipentan-3,-oxy)cyclooctane is isolated by distillation under reduced pressure.

What is claimed is:

1. A method of preparing a dialkoxycycloalkane of the structure (II)

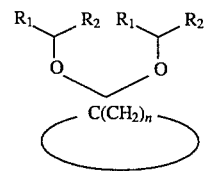

wherein $R_1$ and $R_2$ are different or the same alkyl moiety, said alkyl moiety having from 1 to 3 carbon atoms and n is an integer of from 4 to 9, the method comprising making an imino ether hydrochloride in an organic solvent by anhydrously reacting in the solvent hydrogen cyanide or hydrogen cyanide derivative, hydrogen chloride and a secondary alkanol of the structure (IV)

wherein $R_1$ and $R_2$ correspond to $R_1$ and $R_2$ of structure (II), and anhydrously reacting with the imino ether hydrochloride additional secondary alkanol of the structure (IV) and a cycloalkanone having from 5 to 10 carbon atoms in the ring structure of the cycloalkanone, by adding the additional secondary alkanol in a molar amount equal to at least twice the molar amount of hydrogen cyanide or hydrogen cyanide derivative used to make the imino ether hydrochloride, and adding the cycloalkanone in a molar amount equal to at least the molar amount of hydrogen cyanide or hydrogen cyanide derivative used to make the imino ether hydrochloride.

2. The method of claim 1 wherein the secondary alkanol is added in a molar amount between about 2 and 3 times the molar amount of hydrogen cyanide or hydrogen cyanide derivative used to make the imino ether hydrochloride.

3. The method of claim 1 wherein, while reacting the additional secondary alkanol and cycloalkanone with the imino ether hydrochloride, the solvent is maintained at a temperature of about 20° C. to 50° C.

4. The method of claim 1 and further comprising, prior to reacting the imino ether hydrochloride with the additional secondary alkanol and the cycloalkanone, adjusting the hydrogen chloride concentration in the solvent to about 1% to 5% by weight of the total mixture.

5. The method of claim 4 wherein the hydrogen chloride concentration is adjusted to about 3% by weight of the total mixture.

6. The method of claim 1 wherein the cycloalkanone is added after the additional secondary alkanol has been added to the solvent containing the imino ether hydrochloride.

7. The method of claim 1 and further comprising adjusting the pH of the solvent to within the range of about 2 to 3 prior to reacting the additional secondary alkanol or the cycloalkanone with the imino ether hydrochloride.

8. The method of claim 1 wherein the secondary alkanol is 2-propanol.

* * * * *